US012799536B2

(12) United States Patent
Li et al.

(10) Patent No.: US 12,799,536 B2

(45) Date of Patent: Nov. 17, 2026

(54) TUMOR MARKER STAMP-EP5 BASED ON METHYLATED MODIFICATION

(71) Applicant: SHANGHAI EPIPROBE BIOTECHNOLOGY CO., LTD., Shanghai (CN)

(72) Inventors: Zhenyan Li, Shanghai (CN); Shihua Dong, Shanghai (CN)

(73) Assignee: SHANGHAI EPIPROBE BIOTECHNOLOGY CO., LTD., Shanghai (CN)

( * ) Notice: Subject to any disclaimer, the term of this patent is extended or adjusted under 35 U.S.C. 154(b) by 1383 days.

(21) Appl. No.: 17/309,900

(22) PCT Filed: Dec. 30, 2019

(86) PCT No.: PCT/CN2019/129838

§ 371 (c)(1), (2) Date: Mar. 4, 2022

(87) PCT Pub. No.: WO2020/135862

PCT Pub. Date: Jul. 2, 2020

(65) Prior Publication Data

US 2022/0195528 A1 Jun. 23, 2022

(30) Foreign Application Priority Data

Dec. 29, 2018 (CN) ........................ 201811634957.6

(51) Int. Cl.

*C12Q 1/68* (2018.01)

*C12Q 1/6886* (2018.01)

(52) U.S. Cl.

CPC ..... *C12Q 1/6886* (2013.01); *C12Q 2600/154* (2013.01)

(58) Field of Classification Search

CPC ........................ C12Q 1/6886; C12Q 2600/154

See application file for complete search history.

(56) References Cited

U.S. PATENT DOCUMENTS 8,388,124 B2 3/2013 Gould
8,586,006 B2 11/2013 Hood et al.

FOREIGN PATENT DOCUMENTS

WO WO-9964457 A1 12/1999
WO WO-2010120526 A2 10/2010
WO WO-2012031329 A1 * 3/2012 ........... C12Q 1/6886

OTHER PUBLICATIONS

Bartels (Bartels et al.; PLOS One, vol. 6, pp. 6-10, Oct. 3, 2011) (Year: 2011).*

GenBank Accession No. EF517278 (pp. 1-3, Jul. 2016) (Year: 2016).*

Mah, W., et al., "Methylation profiles reveal distinct subgroup of hepatocellular carcinoma patients with poor prognosis," PLOS ONE 9(8): e104158, Hong Kong, China (published Aug. 2014).

GenBank, "*Homo sapiens* polycystic kidney disease and receptor for egg jelly related protein (PKDREJ) mRNA, complete cds," Accession No. AF116458.1, accessed at https://www.ncbi.nlm.nih.gov/nuccore/AF116458, 4 pages.

Shiraishi, M., et al., "A comprehensive catalog of CpG islands methylated in human lung adenocarcinomas for the identification of tumor suppressor genes," Oncogene 21: 3802-3813, (published 2002).

International Search Report and Written Opinion in International Patent Application No. PCT/CN2019/129838 mailed Apr. 3, 2020, China National Intellectual Property Administration, China, 17 pages (with English translation).

Revill, K., et al., "Genome-wide methylation analysis and epigenetic unmasking identify tumor suppressor genes in hepatocellular carcinoma," Gastroenterology 145(6):1424-1435.e1-25, Elsevier, Netherlands (published online Sep. 2013, published in print Dec. 2013).

* cited by examiner

*Primary Examiner* — Jehanne S Sitton

*Assistant Examiner* — Bailey Buchanan

(74) *Attorney, Agent, or Firm* — STERNE, KESSLER, GOLDSTEIN & FOX P.L.L.C.

(57) ABSTRACT

The present invention provides a methylated tumor marker STAMP-EP5 and an application thereof, relating to the technical field of disease diagnosis markers. The present invention further provides an application of methylated tumor marker STAMP-EP5 in the preparation of tumor diagnostic reagents.

5 Claims, 3 Drawing Sheets

Specification includes a Sequence Listing.

TUMOR MARKER STAMP-EP5 BASED ON METHYLATED MODIFICATION

REFERENCE TO A SEQUENCE LISTING SUBMITTED ELECTRONICALLY VIA EFS-WEB

The content of the electronically submitted sequence listing in ASCII text file (Name: 4790_0040001_Seqlisting_ST25; Size: 4,373 bytes; and Date of Creation: Mar. 4, 2022) is herein incorporated by reference in its entirety.

FIELD OF DISCLOSURE

The disclosure is in the field of disease diagnostic markers. More specifically, the disclosure relates to a methylation based tumor marker STAMP, Specific Tumor Aligned Methylation of Pan-cancer.

BACKGROUND OF DISCLOSURE

Tumors have been considered a genetic disease for decades. Several large-scale systematic sequencings for human have confirmed that the number of somatic mutations in cancer tissues is significantly less than expected. These results suggest that cancer is not a simple genetic disease.

In order to diagnose tumor, many new tumor markers have been discovered and used for clinical diagnosis in recent years. Before 1980, tumor markers were mainly hormones, enzymes, proteins and other cell secretions, such as carcinoembryonic antigen (CEA) and alpha fetoprotein (AFP) used as markers of gastric cancer, liver cancer and other tumors, carbohydrate antigen 125 (CA125) used as a marker of cervical cancer, and prostate specific antigen (PSA) used as a marker of prostate cancer. Although these tumor markers are still used in clinic, their sensitivity and accuracy have been difficult to meet the clinical needs.

More and more evidences show that small changes in epigenetic regulation play an important role in tumors. Epigenetics is a subject that studies that the heritable change of gene function without a change of DNA sequence, which eventually leads to the change of phenotype. Epigenetics mainly includes DNA methylation, histone modification, microRNA level changes and other biochemical processes. DNA methylation is one of the epigenetic mechanisms, refers to the process of transferring methyl from S-adenosylmethionine (methyl donor) to specific bases under the catalysis of DNA methyltransferase (DMT). However, DNA methylation in mammals mainly occurs at the C of 5'-CpG-3', which results in 5-methylcytosine (5 mC).

Fluid biopsy is a technique for the diagnosis and prediction of tumors using circulating tumor cells or circulating tumor DNA as detection targets. The technology has many shortcomings. First, the sensitivity and specificity are not good enough. The tumor itself is heterogeneous, including a variety of subtypes of cell populations. The proportion of tumor DNA in clinical samples, especially blood samples, is very low. The existing tumor markers are difficult to meet the sensitivity of clinical requirements, and it is easy to cause misdiagnosis. Second, one marker has good effect only for one or a few kinds of tumors. As the DNA sources in blood are very complex, the existing tumor markers cannot solve the complex problems of tumor source and metastasis. Because of these complexities, it is difficult for many DNA methylation tumor markers to have a unified standard in clinical application, which seriously affects the sensitivity and accuracy of the markers.

In summary, in the field of tumor diagnosis, it is urgent to discover and study more new tumor markers, so as to provide more possibilities for tumor diagnosis.

SUMMARY OF DISCLOSURE

The object of the disclosure is to provide a method for detecting tumor based on abnormal hypermethylation of specific sites in tumor using DNA methylation modification as a tumor marker.

The first aspect of the present disclosure provides an isolated polynucleotide, including: (a) a polynucleotide with a nucleotide sequence as shown in SEQ ID NO: 1; (b) a fragment of the polynucleotide of (a), having at least one (such as 2-79, more specifically 3, 5, 10, 15, 20, 25, 30, 35, 40, 45, 50, 55, 60, 65, 70, 75) modified CpG site; and/or (c) a nucleic acid (such as the polynucleotide with a nucleotide sequence as shown in SEQ ID NO: 3) complementary to the polynucleotide or fragment of (a) or (b).

In a preferable embodiment, the modification includes 5-methylation(5mC), 5-hydroxymethylation(5hmC), 5-formylcytosine(5fC) or 5-carboxylcytosine (5-caC).

The second aspect of the disclosure provides an isolated polynucleotide, which is converted from the polynucleotide of the first aspect, and as compared with the sequence of the first aspect, the cytosine C of the CpG site(s) with modification is unchanged, and the unmodified cytosine is converted into T or U.

In a preferable embodiment, it is converted from the polynucleotide corresponding to the first aspect by bisulfite treatment. In another preferable embodiment, the polynucleotide includes: (d) a polynucleotide with a nucleotide sequence as shown in SEQ ID NO: 2 or 4; (b) a fragment of the polynucleotide of (d), having at least one (such as 2-79, more specifically 3, 5, 10, 15, 20, 25, 30, 35, 40, 45, 50, 55, 60, 65, 70, 75) CpG site with modification.

The third aspect of the disclosure provides a use of the polynucleotide described in the first or second aspect in manufacture of a tumor detection agent or kit.

In a preferable embodiment, the tumors include (but are not limited to): hematologic cancers such as leukemia, lymphoma, multiple myeloma; digestive system tumors such as esophageal cancer, gastric cancer, colorectal cancer, liver cancer, pancreatic cancer, bile duct and gallbladder cancer; respiratory system tumors such as lung cancer, pleuroma; nervous system tumors such as glioma, neuroblastoma, meningioma; head and neck tumors such as oral cancer, tongue cancer, laryngeal cancer, nasopharyngeal cancer; gynecological and reproductive system tumors such as breast cancer, ovarian cancer, cervical cancer, vulvar cancer, testicular cancer, prostate cancer, penile cancer; urinary system tumors such as kidney cancer, bladder cancer, skin and other systems tumors such as skin cancer, melanoma, osteosarcoma, liposarcoma, thyroid cancer.

In another preferable embodiment, samples of the tumor include but are not limited to: tissue samples, paraffin embedded samples, blood samples, pleural effusion samples, alveolar lavage fluid samples, ascites and lavage fluid samples, bile samples, stool samples, urine samples, saliva samples, sputum samples, cerebrospinal fluid samples, cell smear samples, cervical scraping or brushing samples, tissue and cell biopsy samples.

The fourth aspect of the disclosure provides a method of preparing a tumor detection agent, including: providing the polynucleotide described in the first or second aspect, designing a detection agent for specifically detecting the modification on CPG site(s) of a target sequence which is the full length or fragment of the polynucleotide; wherein, the target sequence has at least one (such as 2-79, more specifically, 3, 5, 10, 15, 20, 25, 30, 35, 40, 45, 50, 55, 60, 65, 70, 75) modified CpG site; preferably, the detection agent includes (but is not limited to) primers or probes.

The fifth aspect of the disclosure provides an agent or a combination of agents which specifically detect the modification on CPG site(s) of a target sequence, which is the full length or fragment of any of the polynucleotides described in the first or second aspect and has at least one (such as 2-79, more specifically, 3, 5, 10, 15, 20, 25, 30, 35, 40, 45, 50, 55, 60, 65, 70, 75) modified CpG site.

In a preferable embodiment, the agent or combination of agents is for a gene sequence containing the target sequence (designed based on the gene sequence), and the gene sequence includes gene Panels or gene groups.

In another preferable embodiment, the detection agent comprises: primers or probes.

In another preferable embodiment, the primers are: the primers shown in SEQ ID NO: 3 and 4; the primers shown in SEQ ID NO: 7 and 8.

In the sixth aspect of the disclosure, a use of the agent or combination of agents described in the fifth aspect of the disclosure in the manufacture of a kit for detecting tumors is provided; preferably, the tumors include (but are not limited to): digestive system tumors such as esophageal cancer, gastric cancer, colorectal cancer, liver cancer, pancreatic cancer, bile duct and gallbladder cancer; respiratory system tumors such as lung cancer, pleuroma; hematologic cancers such as leukemia, lymphoma, multiple myeloma; gynecological and reproductive system tumors such as breast cancer, ovarian cancer, cervical cancer, vulvar cancer, testicular cancer, prostate cancer, penile cancer; nervous system tumors such as glioma, neuroblastoma, meningioma; head and neck tumors such as oral cancer, tongue cancer, laryngeal cancer, nasopharyngeal cancer; urinary system tumors such as kidney cancer, bladder cancer, skin and other systems tumors such as skin cancer, melanoma, osteosarcoma, liposarcoma, thyroid cancer.

The seventh aspect of the present disclosure provides a detection kit, comprising container(s) and the agent or combination of agents described above in the container(s); preferably, each agent is placed in an independent container.

In a preferable embodiment, the kit also includes: bisulfite, DNA purification agent, DNA extraction agent, PCR amplification agent and/or instruction for use (indicating operation steps of the detection and a result judgment standard).

In the eighth aspect of the disclosure, a method for detecting the methylation profile of a sample in vitro is provided, including: (i) providing the sample and extracting the nucleic acid; (ii) detecting the modification on CPG site(s) of a target sequence in the nucleic acid of (i), wherein the target sequence is the polynucleotide described in the first aspect or the polynucleotide converted therefrom as described in the second aspect.

In a preferable embodiment, in step (3), the analysis methods include pyrosequencing, bisulfite conversion sequencing, method using methylation chip, qPCR, digital PCR, second generation sequencing, third generation sequencing, whole genome methylation sequencing, DNA enrichment detection, simplified bisulfite sequencing technology, HPLC, MassArray, methylation specific PCR (MSP), or their combination, as well as in vitro detection and in vivo tracer detection for the combined gene group of partial or all of the methylation sites in the sequence shown in SEQ ID NO: 1. In addition, other methylation detection methods and newly developed methylation detection methods in the future can be applied to the disclosure.

In another preferable embodiment, step (ii) includes: (1) treating the product of (i) to convert the unmodified cytosine into uracil; preferably, the modification includes 5-methylation(5mC), 5-hydroxymethylation(5hmC), 5-formylcytosine(5fC) or 5-carboxylcytosine(5-caC); preferably, treating the nucleic acid of step (i) with bisulfite; and (2) analyzing the modification of the target sequence in the nucleic acid treated by (1).

In another preferable embodiment, the abnormal methylation profile is the high level of methylation of C in CPG(s) of the polynucleotide.

In another preferable embodiment, the methylation profile detecting method is not for the purpose of directly obtaining the diagnosis result of a disease, or is not a diagnostic method.

The ninth aspect of the disclosure provides a tumor diagnosis kit, including primer pairs designed based on the sequence described in the first or second aspect of the disclosure, and gene Panels or gene groups containing the sequence, to obtain the characteristics of normal cells and tumor cells through DNA methylation detection.

Other aspects of the disclosure will be apparent to those skilled in the art based on the disclosure herein.

DETAILED DESCRIPTION

Figure 1:
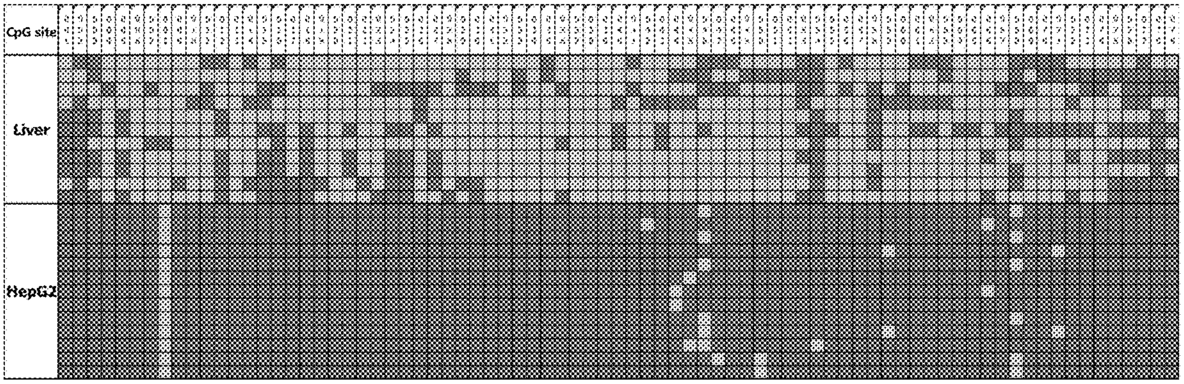
FIG. 1. BSP verification of methylation levels of SEQ ID NO:1 region in liver cancer cells and normal liver cells.

The inventor is committed to the research of tumor markers. After extensive research and screening, the inventor provides a universal DNA methylation tumor marker, STAMP (Specific Tumor Aligned Methylation of Pan-cancer). In normal tissues, STAMP was hypomethylated, while in tumor tissues, it was hypermethylated. It can be used for clinical tumor detection and as the basis of designing tumor diagnostic agents.

Term

As used herein, "isolated" refers to a material separated from its original environment (if the material is a natural material, the original environment is the natural environment). For example, in living cells, polynucleotides and polypeptides in their natural state are not isolated or purified, but the same polynucleotides or polypeptides will be isolated ones if they are separated from other substances existed in the natural state.

As used herein, "sample" includes substances suitable for DNA methylation detection obtained from any individual or isolated tissue, cell or body fluid (such as plasma). For example, the samples include but are not limited to: tissue samples, paraffin embedded samples, blood samples, pleural effusion samples, alveolar lavage fluid samples, ascites and lavage fluid samples, bile samples, stool samples, urine samples, saliva samples, cerebrospinal fluid samples, cell smear samples, cervical scraping or brushing samples, tissue and cell biopsy samples.

As used herein, "hypermethylation" refers to high level of methylation, hydroxymethylation, formylcytosine or carboxylcytosine of CpG in a gene sequence. For example, in the case of methylation specific PCR (MSP), if the PCR reaction with methylation specific primers has positive PCR results, the DNA (gene) region of interest is in hypermethylation state. For another example, in the case of real-time quantitative methylation specific PCR, hypermethylation can be determined based on statistic difference of the methylation status value as compared with the control sample.

As used herein, the tumors include but are not limited to: hematologic cancers such as leukemia, lymphoma, multiple myeloma; digestive system tumors such as esophageal cancer, gastric cancer, colorectal cancer, liver cancer, pancreatic cancer, bile duct and gallbladder cancer; respiratory system tumors such as lung cancer, pleuroma; nervous system tumors such as glioma, neuroblastoma, meningioma; head and neck tumors such as oral cancer, tongue cancer, laryngeal cancer, nasopharyngeal cancer; gynecological and reproductive system tumors such as breast cancer, ovarian cancer, cervical cancer, vulvar cancer, testicular cancer, prostate cancer, penile cancer; urinary system tumors such as kidney cancer, bladder cancer, skin and other systems tumors such as skin cancer, melanoma, osteosarcoma, liposarcoma, thyroid cancer.

Gene Marker

In order to find a useful target for tumor diagnosis, the inventor has identified the target of STAMP-EP5 after extensive and in-depth research. The methylation status of the sequence of STAMP-EP5 gene is significantly different between tumor tissues and non-tumor tissues. If the abnormal hypermethylation of the sequence of STAMP-EP5 gene of a subject is detected, the subject can be identified as having a high-risk of tumor. Moreover, the significant difference of STAMP-EP5 between tumor and non-tumor tissues exists in various types of tumors, including solid tumors and non-solid tumors.

Therefore, the disclosure provides an isolated polynucleotide, comprising the nucleotide sequence shown in the sequence of SEQ ID NO: 1 or SEQ ID NO: 3 (the reverse complementary sequence of SEQ ID NO: 1). For tumor cells, the polynucleotide contains 5-methylcytosine (5mC) at C positions of many 5'-CpG-3'. The disclosure also comprises a fragment of the polynucleotide with a nucleotide sequence as shown in SEQ ID NO: 1 or 3, having at least one (such as 2-79, more specifically 3, 5, 10, 15, 20, 25, 30, 35, 40, 45, 50, 55, 60, 65, 70, 75) methylated CpG site. The above polynucleotides or fragments can also be used in the design of detection agents or detection kits.

In some specific embodiments of the disclosure, the fragment of the polynucleotide are, for example, a fragment containing the residues 242-264 of SEQ ID NO: 1 (containing CpG sites 045-048). A sequence comprising an antisense strand of the above fragment is suitable for the disclosure. These fragments are merely examples of preferable embodiments of the present disclosure. Based on the information provided by the present disclosure, other fragments can also be selected.

In addition, gene Panels or gene groups containing the sequence shown in the SEQ ID NO: 1 or SEQ ID NO: 2 or a fragment thereof is also encompassed by the disclosure. For the gene Panels or gene groups, the characteristics of normal cells and tumor cells can also be identified through DNA methylation detection.

The above polynucleotides can be used as the key regions for analysis of the methylation status in the genome. Their methylation status can be analyzed by various technologies known in the art. Any technique that can be used to analyze the methylation state can be applied to the present disclosure.

When treated with bisulfite, un-methylated cytosine(s) of the above polynucleotides will be converted into uracil, while methylated cytosine(s) remained unchanged.

Therefore, the disclosure also provides the polynucleotides obtained from the above polynucleotides (including the complementary chain (antisense chain)) after being treated with bisulfite, including the polynucleotides with a nucleotide sequence as shown in SEQ ID NO: 2 or SEQ ID NO: 4. These polynucleotides can also be used in the design of detection agents or detection kits.

The disclosure also comprises a fragment of the polynucleotides obtained from the above polynucleotides or the antisense strand thereof after being treated with bisulfite, wherein the fragment contains at least one (such as 2-79, more specifically 3, 5, 10, 15, 20, 25, 30, 35, 40, 45, 50, 55, 60, 65, 70, 75) methylated CpG site. The No. of each CpG site in the antisense strand corresponding to the number of the sense strand is readily obtained according to the content described by the present disclosure.

Detection Agents and Kits

Based on the new discovery of the disclosure, a detection agent designed based on said polynucleotide(s) is also provided for detecting the methylation profile of polynucleotide(s) in the sample in vitro. The detection methods and agents known in the art for determining the sequence, variation and methylation of the genome can be applied in the disclosure.

Therefore, the disclosure provides a method of preparing a tumor detection agent, including: providing the polynucleotide, designing a detection agent for specifically detecting a target sequence which is the full length or fragment of the polynucleotide; wherein, the target sequence has at least one methylated CpG site.

The detection agent herein includes but is not limited to: primers or probes, etc.

For example, the agent are a primer pairs. Based on the sequence of the polynucleotide, those skilled in the art know how to design primer(s). The two primers are on each side of the specific sequence of the target gene to be amplified (including CpG sequence, for the gene region originally methylated, the primer is complementary with CpG, and for the gene region originally un-methylated, the primer is complementary with TpG). It should be understood that based on the new discovery of the disclosure, those skilled in the art can design a variety of primers or probes or other types of detection agents for CpG sites at different positions on the target sequence or their combinations. These primers or probes or other types of detection agents should be included in the technical solution of the disclosure. In preferable embodiment of the present disclosure, the primers are: the primers shown in SEQ ID NO: 5 and 6; or the primers shown in SEQ ID NO: 7 and 8.

The agent can also be a combination of agents (primer combination), including more than one set of primers, so that the multiple polynucleotides can be amplified respectively.

The disclosure also provides a kit for detecting the methylation profile of polynucleotide in a sample in vitro, which comprises container(s) and the above primer pair(s) in the container(s).

In addition, the kit can also include various reagents required for DNA extraction, DNA purification, PCR amplification, etc.

In addition, the kit can also include an instruction for use, which indicates operation steps of the detection and a result judgment standard, for the application of those skilled in the art.

Detection Method

The methylation profile of a polynucleotide can be determined by any technique in the art (such as methylation specific PCR (MSP) or real-time quantitative methylation specific PCR, Methylight), or other techniques that are still developing and will be developed.

Quantitative methylation specific PCR (QMSP) can also be used to detect methylation level. It is a continuous optical monitoring method based on fluorescent PCR, which is more sensitive than MSP. It has high throughput and avoids electrophoresis based result analysis.

Other available technologies include conventional methods in the art such as pyrosequencing, bisulfite converstion sequencing, qPCR, second generation sequencing, whole genome methylation sequencing, DNA enrichment detection, simplified bisulfite sequencing or HPLC, and combined gene group detection. It should be understood that, on the basis of the new disclosure herein, these well-known technologies and some technologies to be developed in the art can be applied to the present disclosure.

As a preferable embodiment of the disclosure, a method of detecting the methylation profile of a polynucleotide in a sample in vitro is also provided. The method is based on the follow principle: the un-methylated cytosine can be converted into uracil by bisulfite, which can be transformed into thymine in the subsequent PCR amplification process, while the methylated cytosine remains unchanged; therefore, after the polynucleotide is treated by bisulfite, the methylated site presents a polynucleotide polymorphism (SNP) similar to C/T. Based on the above principle, methylated and un-methylated cytosine can be distinguished effectively by identifying the methylation profile of a polynucleotide in the sample.

The method of the disclosure includes: (a) providing samples and extracting genomic DNA; (b) treating the genomic DNA of step (a) with bisulfite, so as to convert the un-methylated cytosine in the genomic DNA into uracil; (c) analyzing whether the genomic DNA treated in step (b) contains an abnormal methylation profile.

The method of the disclosure can be used for: (i) analyzing whether a subject has tumor by detecting the sample of the subject; (ii) identifying a population having high-risk of tumor. The method needs not to be aimed at obtaining direct diagnosis results.

In a preferable embodiment of the disclosure, DNA methylation is detected by PCR amplification and pyrosequencing. It should be understood by those in the art that DNA methylation detection is not limited to these methods, and any other DNA methylation detection method can be used. The primers used in PCR amplification are not limited to those provided in Examples.

Because of bisulfite treatment, in which un-methylated cytosine in genomic DNA are converted into uracil and then transformed into thymine in the subsequent PCR process, the sequence complexity of the genome will be reduced, and it will be more difficult to amplify specific target fragments by PCR. Therefore, in order to improve amplification efficiency and specificity, nested PCR may be preferable, wherein two sets of primers (outer primers and inner primers) are used in two successive runs of PCR, and the amplification product from the first run undergoes a second run with the second set of primers. However, it should be understood that the detection methods suitable for the present disclosure are not limited thereto.

After the research and verification on clinical samples, the method of the disclosure provides very high accuracy in the clinical diagnosis of tumors. The disclosure can be applied to the fields of tumor auxiliary diagnosis, efficacy evaluation, prognosis monitoring, etc., thus has a high clinical value.

The disclosure is further illustrated by the specific examples described below. It should be understood that these examples are merely illustrative, and do not limit the scope of the present disclosure. The experimental methods without specifying the specific conditions in the following examples generally used the conventional conditions, such as those described in J. Sambrook, Molecular Cloning: A Laboratory Manual (3rd ed. *Science Press,* 2002) or followed the manufacturer's recommendation.

EXAMPLE 1

Nucleic Acid Sequence for STAMP-EP5 Detection

The sequence of the STAMP-EP5 tumor marker is provided as follows: SEQ ID NO: 1 (chr22:46658718-46659169/hg19), in which the underlined bases are methylated CpG sites, and each number below the underline indicates the site number.

```
CGGCGGAGCGCGGGGAGACGCGGGCCGCGGGGGAGGCCGGGCGGGCGGCGCCGG
01 02  03 04      0506  0708         09  10  11 12 13

GTCCGAGCAGCCGCAGGCGGAAGGCCCAGGCCAGGCGCCCGGGCGAGCGCGGCA
   14      15    16                17  18  10  2021

GCCGCACGGACCACGTCAGGGAGAGGCGGCCGCCGCGCGCGGAGAGCTGCAGGT
  22  23     24           25  26 27282930

CGACGAGCGCGAGCGCGGGCGCGGCCGGCCAGGGCAGGCGTTGGGCGCTGAGCA
31 32  3334  3536  3738  39           40     41
```

-continued

GGACGCGCAAGTCGAGGCAGTACCAGCGCCGCCCGGTCCCGCCATGGGGGAAGC
4243 44 45 46 47 48

AGAGGCTGGCGCGGCCGCTCAGGACAGCGCCGCCCGCCCGCACCGCGGTGGGCCG
4950 51 52 53 54 55 5657 58

CAGACTGAGGAGGGCGCGGCCGCCGCGCACCCCGAGGCCCGGGGGCGCCCCTGAG
5960 61 6263 64 65 66

GAGGCCACCGGGCGCCCCGGAGACGGCGGCTTGTGCCCCGCGAGGAACCGGCGG
67 68 69 70 71 7273 74 75

CAGCGGGAGGCGGCCGACG
76 77 78 79

The bisulfite treated sequence of SEQ ID NO: 1 is shown in SEQ ID NO: 2 (Y represents C or U) as follows:

YGGYGGAGYGYGGGGAGAYGYGGGUYGYGGGGGAGGUYGGGYGGGYGGYGUYGG
01 02 03 04 0506 0708 09 10 11 12 13

GTUYGAGUAGUYGUAGGYGGAAGGUUUAGGUUAGGYGUUYGGGYGAGYGYGGUA
14 15 16 17 18 10 2021

GUYGUAYGGAUUAYGTUAGGGAGAGGYGGUYGUYGYGYGYGGAGAGUTGUAGGT
22 23 24 25 26 27282930

YGAYGAGYGYGAGYGYGGGYGYGGUYGGUUAGGGUAGGYGTTGGGYGUTGAGUA
31 32 3334 3536 3738 39 40 41

GGAYGYGUAAGTYGAGGUAGTAUUAGYGUYGUUYGGTUUYGUUATGGGGGAAGU
4243 44 45 46 47 48

AGAGGUTGGYGYGGUYGUTUAGGAUAGYGUYGUUYGUUYGUAUYGYGGTGGGUYG
4950 51 52 53 54 55 5657 58

UAGAUTGAGGAGGGYGYGGUYGUYGYGUAUUUYGAGGUUYGGGGGYGUUUUTGAG
5960 61 6263 64 65 66

GAGGUUAUYGGGYGUUUYGGAGAYGGYGGUTTGTGUUUYGYGAGGAAUYGGYGG
67 68 69 70 71 7273 74 75

UAGYGGGAGGYGGUYGAYG
76 77 78 79

The reverse complementary sequence of SEQ ID NO: 1 is shown in SEQ ID NO: 3 as follows:

CGTCGGCCGCCTCCCGCTGCCGCCGGTTCCTCGCGGGGCACAA
GCCGCCGTCTCCGGGGCGCCCGGTGGCCTCCTCAGGGGCGCCC
CGGGCCTCGGGGTGCGCGGCGGCCGCGCCCTCCTCAGTCTGCG
GCCCAGCGCGGTGCGGGCGGGCGGCGCTGTCCTGAGCGGCCG
CGGCAGCCTCTGCTTCCCCCATGGCGGGACCGCGCGGCGCTG
GTACTGCCTCGACTTGCGCGTCCTGCTCAGCGCCCAACGCCT
GCCCTGGCCGGCCGCGCCCGCGCTCGCGCTCGTCGACCTGCA
GCTCTCCGCGCGCGGCGGCCGCCTCTCCCTGACGTGGTCCGT
GCGGCTGCCGCGCTCGCCCGGGCGCCTGGCCTGGGCCTTCCG
CCTGCGGCTGCTCGGACCCGGCGCCGCCCGCCCGGCCTCCCC
CGCGGCCCGCGTCTCCCCGCGCTCCGCCG

The bisulfite treated sequence of SEQ ID NO: 3 is shown in SEQ ID NO: 4 (Y represents C or U) as follows:

YGTYGGUYGUUTUUYGUTGUYGUYGGTUUTYGYGGGGUAUA
AGUYGUYGTUTUYGGGGYGUUYGGTGGUUTUUTUAGGGGYGU
UUYGGGUUTYGGGGTGYGYGGYGGUYGYGUUUTUUTUAGTUT
GYGGUUUAGYGYGGTGYGGGYGGGYGGYGUTGTUUTGAGYGG
UYGYGGUAGUUTUTGUTTUUUUUATGGYGGGAUYGGGYGGYG
UTGGTAUTGUUTYGAUTTGYGYGTUUTGUTUAGYGUUUAAYG
UUTGUUUTGGUYGGUYGYGUUYGYGUTYGYGUTYGTYGAUUT
GUAGUTUTUYGYGYGYGGYGGUYGUUTUTUUUTGAYGTGGTU
YGTGYGGUTGUYGYGUTYGUUYGGGYGUUTGGUUTGGGUUTT
UYGUUTGYGGUTGUTYGGAUUYGGYGUYGUUYGUUYGGUUTU
UUUYGYGGUUYGYGTUTUUUYGYGUTUYGUYG

EXAMPLE 2

Difference in Methylation of STAMP-EP5 CpG Sites Between Tumor Cells and Non-Tumor Cells—Bisulfite Sequencing PCR (BSP)

1. Genomic DNA was extracted from liver cancer cell line HepG2 and normal liver cell line;

2. The extracted genomic DNA of HepG2 and normal liver cell lines were treated with bisulfite and used as templates for subsequent PCR amplification;

3. Primers (SEQ ID NO: 5-6; Table 1)were designed according to SEQ ID NO: 1 by conventional methods for amplification;

4. After PCR amplification, 2% agarose gel electrophoresis was used to detect the specificity of the PCR fragments. The target fragments were recovered by gel cutting and connected to T vector which was transformed into competent *Escherichia coli*. The bacteria were spread on plate, and clones were selected the next day and sequenced. Ten clones were selected for each fragment for Sanger sequencing.

TABLE 1

| BSP primer | | |
|---|---|---|
| Primer Name | 5'-3' Primer Sequence | Detected CpG site No. |
| STAMP-EP5-Sanger-Primer-F | GAAGTTTTGTTGGGGTYGYGGGTTTGG (SEQ ID NO: 5) | CpG 001-079 of the above SEQ ID NO: 1 |
| ST AMP-EP5-Sanger-Primer-R | CTCCTCCTTCTAAACRTAAACCTAAACCTAA (SEQ ID NO: 6) | |

BSP verification of methylation levels of SEQ ID NO:1 region in liver cancer cells and normal liver cells is shown in FIG. 1, which indicates that the methylation level of STAMP-EP5 of liver cancer cells is significantly higher than that of normal liver cells. SEQ ID NO: 1 is useful as a diagnosis marker.

EXAMPLE 3

Difference in Methylation of STAMP-EP5 CpG Sites Between Tumor Cells and Non-Tumor Cells—Pyrosequencing 1. Clinical samples: paracancerous/non-cancer were used as the control group, and cancer tissue samples were used as the experimental group;

2. DNA extraction: DNA was extracted from the experimental group and the control group respectively. Phenol-chloroform extraction method was used in this experiment, which is not limited thereto;

3. Bisulfite treatment: the extracted DNA samples were treated with bisulfite and the procedures were strictly followed. EZ DNA Methylation-Gold Kit (ZYMO Research, Cat #D5006) was used in this experiment, which is not limited thereto;

4. Primer design: PCR primers and pyrosequencing primers were designed according to the characteristics of SEQ ID NO: 1 of STAMP-EP5 sequence. The methylation values of STAMP-EP5 were detected as the methylation values of CpG sites 045-048. The PCR primers sequences, pyrosequencing primers sequences, and the pyrosequencing detecting sequences and the detected sites are shown as SEQ ID NO: 7-10 (Table 2);

5. PCR amplification and agarose gel electrophoresis: The bisulfite treated samples were used as templates for PCR amplification. The specificity of PCR amplification was identified by agarose gel electrophoresis of the amplified products;

6. Pyrosequencing: Pyro Mark Q96 ID pyrosequencing instrument (QIAGEN) was used for sequencing, and the procedures in instructions were strictly followed;

7. Calculation of STAMP-EP5 methylation value: pyrosequencing can detect the methylation value of each site in the target region, respectively, and the average methylation value of all sites were calculated as the STAMP-EP5 methylation value in the sample;

8. Results analysis: the methylation value of STAMP-EP5 was compared between the paracancerous/non-cancer control group and the cancer experimental group.

TABLE 2

| Pyro primer | | |
|---|---|---|
| Primer Name | 5'-3' sequence | Remark |
| STAMP-EP5-Pyroseq-Primer-F | GGTTAGGGTAGGYGTTGGGYGTTGAGTAGGA (SEQ ID NO: 7) | The primer pair detects CpG 045-048 of SEQ ID NO: 1 |
| STAMP-EP5-Pyroseq-Primer-R (modified by 5'-Biotin) | CRACAACCTCTACTTCCCCCATAAC (SEQ ID NO: 8) | |
| STAMP-EP5-Pyroseq-Primer-Seq | AGTAGGAYGYGTAAGTYGAGGTAGTATTAG (SEQ ID NO: 9) | |
| pyrosequencing detecting sequences | YGTYGTTYGGTTTYGTTATGGGGGAAGTAGAGGTTGTYGT (SEQ ID NO: 10) | |

EXAMPLE 4

STAMP-EP5: Breast Cancer—Clinical Sample Assay—Pyrosequencing

STAMP-EP5 methylation value between the control group of 5 cases of breast cancer paracancerous clinical samples and the experimental group of 5 cases of breast cancer clinical samples was compared according to the pyrosequencing described in Example 3.

Figure 2:
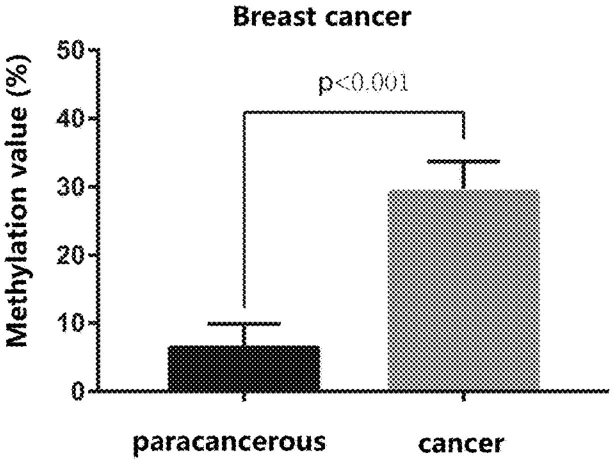
FIG. 2. In clinical samples of breast cancer, the methylation value of STAMP-EP5 in the experimental group was significantly higher than that of paracancerous tissues; $p<0.001$.

The result in FIG. 2 shows that, in clinical samples of breast cancer, the methylation value of STAMP-EP5 in the experimental group was significantly higher than that of paracancerous tissues.

EXAMPLE 5

STAMP-EP5: Leukemia Clinical Sample Assay—Pyrosequencing

STAMP-EP5 methylation value between the control group of 8 non-leukemia bone marrow smear clinical samples and the experimental group of 8 leukemia bone marrow smear clinical samples was compared according to the pyrosequencing described in Example 3.

Figure 3:
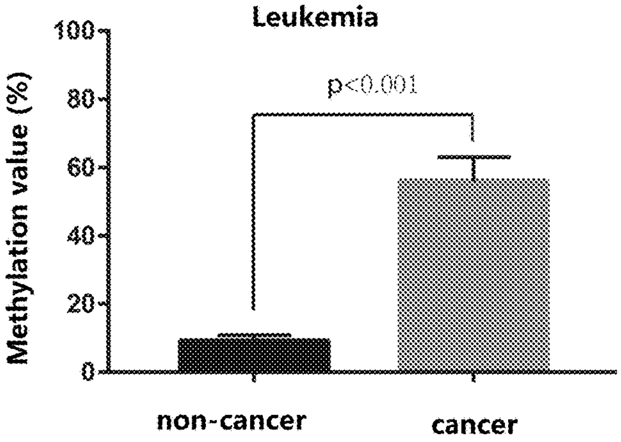
FIG. 3. In clinical samples of leukemia, the methylation value of STAMP-EP5 in the experimental group was significantly higher than that of non-cancer tissues; $p<0.001$.

The result in FIG. 3 shows that, in clinical samples of leukemia, the methylation value of STAMP-EP5 in the experimental group was significantly higher than that of non-cancer tissues.

EXAMPLE 6

STAMP-EP5: Colorectal Cancer—Clinical Sample Assay—Pyrosequencing

STAMP-EP5 methylation value was analyzed on the control group of 8 cases of colorectal cancer paracancerous clinical samples and the experimental group of 8 cases of colorectal cancer clinical samples according to the pyrosequencing described in Example 3.

Figure 4:
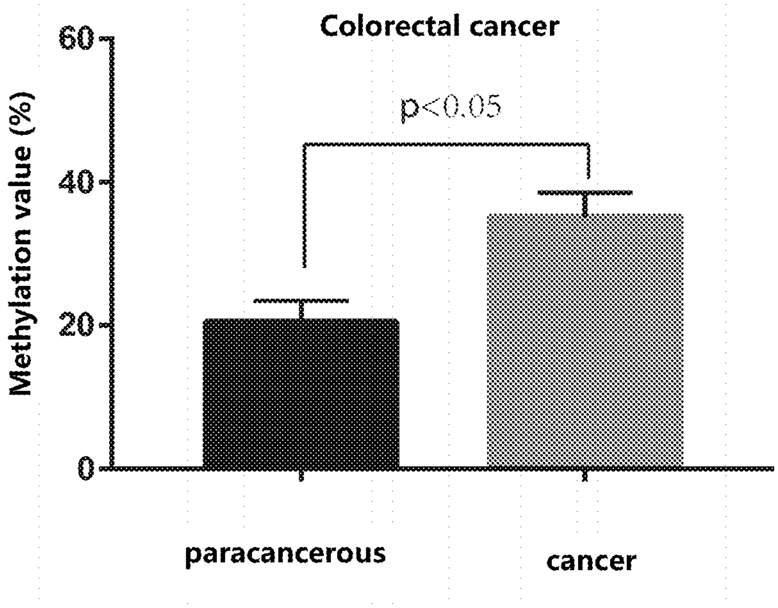
FIG. 4. In clinical samples of colorectal cancer, the methylation value of STAMP-EP5 in the experimental group was significantly higher than that of paracancerous tissues; $p<0.01$.

The result in FIG. 4 shows that, in clinical samples of colorectal cancer, the methylation value of STAMP-EP5 in the experimental group was significantly higher than that of paracancerous tissues.

EXAMPLE 7

STAMP-EP5: Liver Cancer Clinical Sample Assay—Pyrosequencing

STAMP-EP5 methylation value was analyzed on the control group of 8 cases of liver cancer paracancerous clinical samples and the experimental group of 8 cases of liver cancer clinical samples according to the pyrosequencing described in Example 3.

Figure 5:
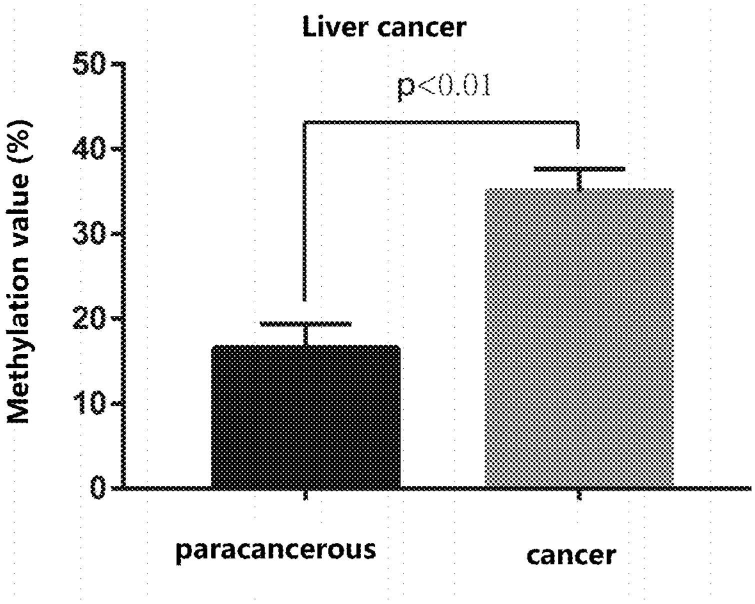
FIG. 5. In clinical samples of liver cancer, the methylation value of STAMP-EP5 in the experimental group was significantly higher than that of paracancerous tissues; $p<0.05$.

The result in FIG. 5 shows that, in clinical samples of liver cancer, the methylation value of STAMP-EP5 in the experimental group was significantly higher than that of paracancerous tissues.

EXAMPLE 8

STAMP-EP5: Lung Cancer Clinical Sample Assay—Pyrosequencing

STAMP-EP5 methylation value was analyzed on the control group of 4 cases of lung cancer paracancerous clinical samples and the experimental group of 4 cases of lung cancer clinical samples according to the pyrosequencing described in Example 3.

Figure 6:
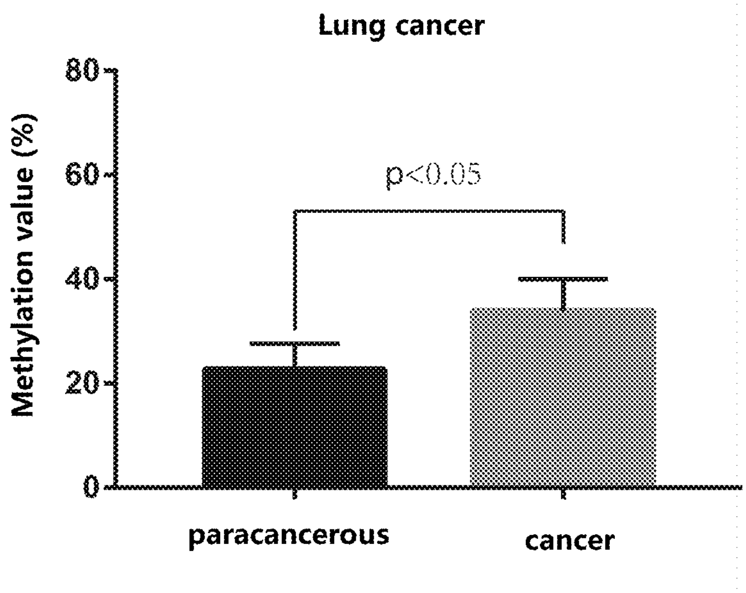
FIG. 6. In clinical samples of lung cancer, the methylation value of STAMP-EP5 in the experimental group was significantly higher than that of paracancerous tissues; $p<0.001$.

The result in FIG. 6 shows that, in clinical samples of lung cancer, the methylation value of STAMP-EP5 in the experimental group was significantly higher than that of paracancerous tissues.

EXAMPLE 9

STAMP-EP5: Pancreatic Cancer—Clinical Sample Assay—Pyrosequencing

STAMP-EP5 methylation value was analyzed on the control group of 4 cases of pancreatic cancer paracancerous clinical samples and the experimental group of 4 cases of pancreatic cancer clinical samples according to the pyrosequencing described in Example 3.

Figure 7:
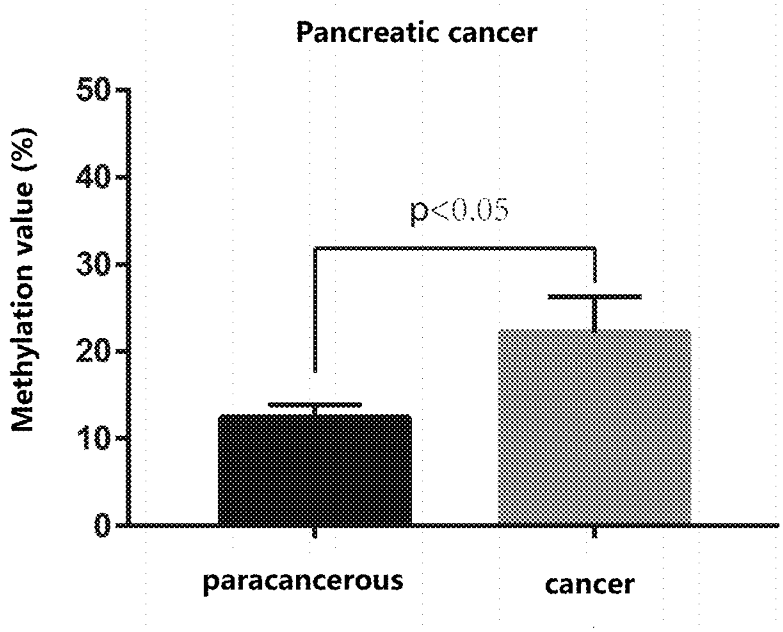
FIG. 7. In clinical samples of pancreatic cancer, the methylation value of STAMP-EP5 in the experimental group was significantly higher than that of paracancerous tissues; $p<0.01$.

The result in FIG. 7 shows that, in clinical samples of pancreatic cancer, the methylation value of STAMP-EP5 in the experimental group was significantly higher than that of paracancerous tissues.

Each reference provided herein is incorporated by reference to the same extent as if each reference was individually incorporated by reference. In addition, it should be understood that based on the above teaching content of the disclosure, those skilled in the art can practice various changes or modifications to the disclosure, and these equivalent forms also fall within the scope of the appended claims.

We claim:

1. A method for detecting one or more cancers in a subject comprising:

treating DNA extracted from one or more samples comprising tumor cells with a reagent that modifies DNA in a methylation-specific manner; and detecting a methylation modification on a CpG site of a polynucleotide using a tumor detection agent or kit;

wherein the polynucleotide consists of residues 242-264 of SEQ ID NO: 1;

wherein the one or more cancers are selected from breast cancer, colorectal cancer, liver cancer, lung cancer, and pancreatic cancer.

2. The method according to claim 1, wherein the one or more samples comprise: tissue samples, paraffin embedded samples, blood samples, pleural effusion samples, alveolar lavage fluid samples, ascites and lavage fluid samples, bile samples, stool samples, urine samples, saliva samples, sputum samples, cerebrospinal fluid samples, cell smear-samples, cervical scraping or brushing samples, and cell biopsy samples.

3. A method of preparing a detection agent, comprising: providing the polynucleotide of claim 1 and designing a detection agent for specifically detecting a target sequence which is the full length or fragment of the polynucleotide; wherein, the target sequence has at least one modified CpG site and wherein the detection agent preferably comprises: primers or probes.

4. The method according to claim 1, further comprising analyzing the modification by pyrosequencing, bisulfite conversion sequencing, method using methylation chip, qPCR, digital PCR, second generation sequencing, third generation sequencing, whole genome methylation sequencing, DNA enrichment detection, simplified bisulfite sequencing technology, HPLC, MassArray, methylation specific PCR, or by in vitro detection and in vivo detection for a combined gene group of partial or all of the methylation sites in residues 242-264 of SEQ ID NO: 1.

5. The method according to claim 1, wherein treating DNA extracted from one or more samples further comprises:

(1) treating extracted nucleic acid to convert unmodified cytosine into uracil; wherein detected modifications preferably include 5-methylation, 5-hydroxymethylation, 5-formylcytosine or 5-carboxylcytosine and wherein treatment is preferably treatment with bisulfite; and (2) analyzing the modification of the target sequence in the nucleic acid treated by (1).

* * * * *

SEQUENCE LISTING

```
<160> NUMBER OF SEQ ID NOS: 10

<210> SEQ ID NO 1
<211> LENGTH: 452
<212> TYPE: DNA
<213> ORGANISM: Homo sapiens

<400> SEQUENCE: 1

cggcggagcg cggggagacg cgggccgcgg gggaggccgg gcgggcggcg ccgggtccga      60

gcagccgcag gcggaaggcc caggccaggc gcccgggcga gcgcggcagc cgcacggacc     120

acgtcaggga gaggcggccg ccgcgcgcgg agagctgcag gtcgacgagc gcgagcgcgg     180

gcgcggccgg ccagggcagg cgttgggcgc tgagcaggac gcgcaagtcg aggcagtacc     240

agcgccgccc ggtcccgcca tgggggaagc agaggctgcc gcggccgctc aggacagcgc     300

cgcccgcccg caccgcgctg ggccgcagac tgaggagggc gcggccgccg cgcaccccga     360

ggcccggggc gcccctgagg aggccaccgg gcgccccgga gacggcggct tgtgccccgc     420

gaggaaccgg cggcagcggg aggcggccga cg                                   452


<210> SEQ ID NO 2
```

<211> LENGTH: 452
<212> TYPE: DNA
<213> ORGANISM: Artificial Sequence
<220> FEATURE:
<223> OTHER INFORMATION: polynucleotide treated with bisulfite

<400> SEQUENCE: 2
yggyggagyg yggggagayg yggguygygg gggagguygg gyggggyggyg uygggtuyga 60 guaguyguag gyggaagguu uagguuaggy guuygggyga gygygguagu yguayggauu 120
aygtuaggga gaggygguyg uygygygygg agagutguag gtygaygagy gygagygygg 180
gygygguygg uuaggguagg ygttgggygu tgaguaggay gyguaagtyg agguagtauu 240
agyguyguuy ggtuuyguua tgggggaagu agaggutguy gygguygutu aggauagygu 300
yguuyguuyg uauygygutg gguyguagau tgaggagggy gygguyguyg yguauuuyga 360
gguuyggggy guuuutgagg agguuauygg gyguuuygga gayggyggut tgtguuuygy 420
gaggaauygg ygguagyggg aggygguyga yg 452

<210> SEQ ID NO 3
<211> LENGTH: 452
<212> TYPE: DNA
<213> ORGANISM: Homo sapiens

<400> SEQUENCE: 3
cgtcggccgc ctcccgctgc cgccggttcc tcgcggggca caagccgccg tctccggggc 60
gcccggtggc ctcctcaggg gcgccccggg cctcggggtg cgcggcggcc gcgccctcct 120
cagtctgcgg cccagcgcgg tgcgggcggg cggcgctgtc ctgagcggcc gcggcagcct 180
ctgcttcccc catggcggga ccgggcggcg ctggtactgc ctcgacttgc gcgtcctgct 240
cagcgcccaa cgcctgccct ggccggccgc gcccgcgctc gcgctcgtcg acctgcagct 300
ctccgcgcgc ggcggccgcc tctccctgac gtggtccgtg cggctgccgc gctcgcccgg 360
gcgcctggcc tgggccttcc gcctgcggct gctcggaccc ggcgccgccc gcccggcctc 420
ccccgcggcc cgcgtctccc cgcgctccgc cg 452

<210> SEQ ID NO 4
<211> LENGTH: 452
<212> TYPE: DNA
<213> ORGANISM: Artificial Sequence
<220> FEATURE:
<223> OTHER INFORMATION: polynucleotide treated with bisulfite

<400> SEQUENCE: 4
ygtygguygu utuuygutgu yguyggttuu tygyggggua uaaguyguyg tutuyggggy 60
guuyggtggu utuutuaggg gyguuuyggg uutyggggtg ygyggyggu gyguuutuut 120 uagtutgygg uuuagygygg tgygggyggg yggygutgtu utgagyggu gygguaguut 180 utguttuuuu uatggygga uygggyggyg utggtautgu utygauttgy gygtuutgut 240
uagyguuuaa yguutguuut gguygguygy guuygyguty gygutygtyg auutguagut 300
utuygygygy ggygguyguu tutuuutgay gtggtuygtg yggutguygy gutyguuygg 360
gyguutgguu tggguuttuy guutgyggut gutyggauuy ggyguyguuy guuygguutu 420
uuuygygguu ygygtutuuu ygygutuygu yg 452

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
gaagttttgt tggggtygyg ggtttgg 27

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
ctcctccttc taaacrtaaa cctaaaccta a 31

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
ggttagggta ggygttgggy gttgagtagg a 31

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
cracaacctc tacttccccc ataac 25

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
agtaggaygy gtaagtygag gtagtattag 30

<210> SEQ ID NO 10
<211> LENGTH: 40
<212> TYPE: DNA
<213> ORGANISM: Artificial Sequence
<220> FEATURE:
<223> OTHER INFORMATION: Primer

<400> SEQUENCE: 10
ygtygttygg tttygttatg ggggaagtag aggttgtygt 40